United States Patent [19]

Gaenzler et al.

[11] 3,960,934

[45] June 1, 1976

[54] METHOD FOR THE OXYCARBONYLATION OF ETHYLENE AND PROPYLENE

[75] Inventors: Wolfgang Gaenzler, Darmstadt-Arheilgen; Klaus Kabs, Seeheim; Guenter Schroeder, Ober-Ramstadt, all of Germany

[73] Assignee: Rohm GmbH, Darmstadt, Germany

[22] Filed: Mar. 24, 1975

[21] Appl. No.: 561,633

[30] Foreign Application Priority Data

Apr. 1, 1974 Germany.............................. 2415742

[52] U.S. Cl. ........................ 260/484 R; 260/485 R; 260/486 AC; 260/497 R
[51] Int. Cl.² .................... C07C 69/54; C07C 69/66
[58] Field of Search ...... 260/484 R, 486 AC, 485 R

[56] References Cited

UNITED STATES PATENTS

| | | | |
|---|---|---|---|
| 3,397,225 | 8/1968 | Fenton | 260/486 AC |
| 3,397,226 | 8/1968 | Fenton | 260/496 AC |

*Primary Examiner*—Paul J. Killos
*Attorney, Agent, or Firm*—Curtis, Morris & Safford

[57] ABSTRACT

A process for the catalytic oxycarbonylation of ethylene and propylene by reaction with carbon monoxide and oxygen in a methanolic or ethanolic reaction medium employing a catalyst which contains a compound of vanadium, chromium, iron, cobalt, nickel or copper and chloride, bromide, or iodide ions.

34 Claims, No Drawings

METHOD FOR THE OXYCARBONYLATION OF ETHYLENE AND PROPYLENE

The present invention relates to a process for the catalytic oxidative carbonylation of ethylene and propylene in an alcoholic medium, whereby the methyl or ethyl ester pf acrylic acid or methacrylic acid, or other esters which can be converted into the aforementioned acrylic acid and methacrylic acud esters by methods known in the art, are formed.

It is known from U.S. Pat. No. 3,397,226 that the reaction of an olefin in an alcohol, termed oxycarbonylation, leads to the production of esters of saturated and unsaturated carboxylic acids if the reaction takes place in the presence of a catalyst comprising a platinum metal and the salt of a varivalent metal which has a more positive oxidation potential than the platinum metal. Copper is mentioned as the preferred redox metal. In the simplest embodiment, the invention according to this patent is carried out by reacting ethylene in methanol with carbon monoxide and oxygen in the presence of a catalyst comprising palladium, copper, and a halogen. The reaction products resulting therefrom are methyl acrylate, succinic acid dimethyl ester, and methyl-$\beta$-methoxypropionate. If propylene is substituted for the ethylene, according to this patent crotonic acid methyl ester, $\beta$-alkoxy-butyrate, and pyrotartrate are produced. The oxycarbonylation according to U.S. Pat. No. 3,397,226 is carried out at temperatures between 0°C. and 300°C. and at a pressure of up to almost 200 atmospheres. It is to be carried out in an essentially anhydrous medium.

The regeneration of a catalyst containing a platinum metal, preferably palladium, is of particular significance in view of the value of the platinum metals. Such a regeneration is therefore described in this patent in detail.

Concerning the mechanism of the oxycarbonylation of olefins in the presence of an alcohol, the inventor discloses that the platinum metal present in the catalyst is reduced during the reaction to a lower oxidation state and thereafter is again reoxidized by the redox component of the catalyst, for example copper or quinone. According to the teachings of the inventor, the presence of a halogen simplifies the oxidation of the platinum metal, which is present as an ion.

The discussion of the mechanism of the oxycarbonylation of olefins in the presence of an alcohol present in U.S. Pat. No. 3,397,226, as well as in U.S. Pat. No. 3,397,225 issued on the same day therewith, agrees with the explanation for the formation of ethylene carboxylic acids from an olefin, oxygen, and carbon monoxide in, for example, glacial acetic acid, given in German Offenlegungsschrift, 1,493,375, namely that interaction between a platinum metal and a redox component is a critical requirement. Thus, it seemed sure that a catalyst system promoting oxycarbonylation must, on the one hand, contain a platinum metal and, on the other hand, a redox component. This teaching has oriented the thought of those researchers working in this field since the appearance of the basic publications concerning the oxycarbonylation of olefins.

According to the present invention, it is demonstrated that, surprisingly, catalysts which do not correspond to the principle of composition heretofore thought critical promote the oxycarbonylation of olefins in the presence of an alcohol, with the formation of saturated and unsaturated carboxylic acid esters, in an exceptional manner.

The oxycarbonylation of an olefin in an alcohol in the presence of a compound of a platinum metal, advantageously with the addition of copper-II-chloride, is described in German Offenlegungsschrift 1,568,778, corresponding to U.S. Pat. No. 3,579,568.

It has now been found that ethylene and propylene in methanol or ethanol, under pressure, at elevated temperatures, and in the presence of a catalyst soluble in the reaction medium can be reacted with carbon monoxide and oxygen with the direct production of acrylic acid- or methacrylic acidmethyl ester or ethyl ester and/or with the production of the methyl ester of $\beta$-hydroxy-propionic acid or $\beta$-methoxy-propionic acid and/or the methyl ester of $\beta$-hydroxybutyric acid- or $\beta$-methoxybutyric acid and/or (methyl-) succinic acid dimethyl ester, or the corresponding ethyl esters or $\beta$-ethoxyethyl esters, if the oxycarbonylation is carried out in the presence of a compound of vanadium, chromium, iron, cobalt, nickel, or copper. Further, to the extent that the aforementioned metals are not themselves employed as their halides, also the systems contain a chloride, bromide, or iodide.

Several of the aforementioned metals and several of the aforementioned halides may be present in the catalytically effective systems of the invention.

As is further evident from Examples 1 and 2 herein, systems can also be employed which, in addition to the aforementioned metals, optionally contain a compound of a further metal such as titanium, magnesium, aluminum, or niobium. These systems, however, critically must contain at least one of the catalyst metals vanadium, chromium, iron, cobalt, nickel, or copper in order to promote oxycarbonylation.

The new catalysts have a number of advantages in comparison with the known palladium catalysts: the working up of the catalyst which is required because of cost when palladium containing catalysts are employed can in many cases be omitted. Further, the catalysts do not promote the formation of aldehydes or ketones, whereas the known palladium-copper catalysts promote the oxidation of olefins to the formation of just such products.

It can be hypothesized that the metal compounds employed in the preparation of the catalysts of the present invention form complexes under the reaction conditions of the oxycarbonylation, which complexes act as homogeneous catalysts. However, even if no complete explanation has been developed for the structure of these complexes, it can be hypothesized that the catalytic mechanism of ester formation according to the invention is one other than that which has heretofore been assumed to be operative in processes promoted by a palladium-copper catalyst. As described by Fenton and Olivier in CHEMTECH, 220 – 225 (1972), the catalysts heretofore known operate by the continuous oxidation-reduction exchange between platinum and a heavy metal. Further to this, it can be presumed that, as described above, the metals to be employed as catalysts according to the present invention are present, as ions, as the central atom of a multinuclear complex in which, under the reaction conditions, olefin molecules and carbonyl groups appear as ligands. Also, it is highly probable that the halides which are to be employed according to the present invention are present as ligands in the formation of the catalytically-effective complexes.

For increasing the selectively and reactivity of the new catalysts, the optional presence, in the reaction mixture, of phosphites, of nitrogen oxides, of heterocyclic tertiary amines, of phosphines, or of phosphine oxides can be advantageous. Among these compounds, the trialkylphosphites, suitably having up to 12 carbon atoms, triphenyl phosphine, trialkyl, trialkylol, and tri(alkylphenyl) phosphines having up to 4 carbon atoms in the alkyl portion thereof, phosphine oxides of the aforementioned phosphines, pyridine, and pyridine-N-oxide can be mentioned as particularly advantageous. Especially preferred materials are the tri-($C_1$-$C_4$)-alkyl phosphines, triphenyl phosphine, tritolyl phosphine, triphenylphosphine oxide, and tri-(hydroxymethyl) phosphine oxide.

It can be presumed that the aforementioned compounds are also present as ligands in a complex. As known in the art, ligands, because of their pi-acceptor strength, loosen the bonding of other groups to the complex and promote their dissociative removal. The result of this is the creation of free reaction-orbitals necessary for catalysis. The activity of a metal-containing catalyst is known to depend on the oxidation state of the metal and of the nature of the ligands. Therefore, it is understandable that the metal complexes which may be present according to the present invention are advantageous catalysts, since the metals in question appear in several oxidation states and, further, are capable of forming complexes with a large number of ligands.

Carbon monoxide and oxygen can in principle be reacted in stoichiometric amounts with the olfin, as illustrated for the case of ethylene by the following reaction equation:

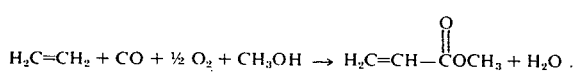

Nevertheless, the use of stoichiometric quantities is not always suitable. More often, carbon monoxide is employed in considerable excess. Likewise, the olefin may also be present in excess. In order to avoid the formation of explosive mixtures, oxygen is preferably continuously introduced in measure with its consumption, which is also the case even if the process is not carried out in a fully continuous manner. The introduction of oxygen, which can be employed in the form of air, preferably taks place such that the oxygen content of the exit gas is kept under the explosive concentration limit, i.e. less than about 10 volume percent, and preferably less than about 3 volume percent. The excess gas, principally comprising olefin and carbon monoxide, can be reintroduced into the liquid reaction medium.

Ester formation according to the present invention can be carried out in a temperature range from 80°C. to 300°C. The aforementioned reaction equation shows that the formation of ester is promoted by the use of pressure, and operation under pressure is indicated also for maintaining liquid phase conditions. Thus, the reaction is carried out under superatmospheric pressure, advantageously under a pressure of from 1 – 200 atmospheres gauge. It should be mentioned that the process can be carried out continuously or discontinuously.

The new metal catalysts are employed in the form of compounds soluble in methanol or ethanol or soluble in the reaction medium and under the reaction conditions. This embodiment of the invention is preferred to carrying out oxycarbonylation in the gas phase with the use of a catalyst according to the present invention present on an inert carrier, although such a process is possible in principle.

The new catalysts can be prepared in different ways. Techniques for the preparation of the catalysts are described in detail in the Examples, in part with reference to pertinent literature. The amount of the novel catalyst to be employed can vary over wide limits in dependence on its specific activity and on the other reaction conditions and, in general, may be between 0.01 and 5 percent by weight of the liquid medium. The requirement that the catalysts, in addition to containing a compound of one of the aforementioned metals, also contain a chloride, bromide, or iodide, is fulfilled if one employs a halide (with the exception of the fluoride) of one of the aforementioned metals in preparing the catalysts. However, as is shown in Example 4, it is also possible to use a halide of a non-catalytic metal, preferably an alkali halide, in the preparation of the metal complexes.

As already described, in the oxycarbonylation of ethylene and propylene according to the present invention, the following products are obtained in different proportions depending on the catalyst system employed and the reaction conditions: (a) (meth-)acrylic acid methyl ester and/or (b) β-hydroxy propionic acid methyl ester or β-methoxy-propionic acid methyl ester and/or β-hydroxybutyric acid methyl ester or β-methoxybutyric acid methyl ester and/or (c) (methyl-)succinic acid dimethyl ester, as well as the corresponding ethyl and β-ethoxyethyl esters. The esters mentioned under (b) and (c) above can be employed as such, for example as solvents or solvent mixtures, or can be converted by conventional methods into the corresponding acrylic acid esters or methyacrylic acid esters.

German patent No. 1,125,915 teaches the preparation of acrylic acid esters by the cleavage of alcohol from β-alkoxy monocarboxylic acid esters. For example, a β-methoxy isobutyric acid ester is conducted in vapor form, at 370°C. – 390°C., over a catalyst comprising silicic acid and 5 – 30 percent of alkali metal silicates or alkaline earth metal silicates. Methacrylic acid ester is obtained in good yield by the cleavage of methanol.

According to German patent No. 1,126,378, acrylic acid esters and methacrylic acid esters are prepared from β-alkoxypropionic acid esters or β-alkoxyisobutyric acid esters by conducting them in vapor form, at 180°C. – 270°C., over boron phosphate which may optionally be present on a silicic acid gel as a carrier.

The preparation of acrylic acid esters from β-alkoxy monocarboxylic acid esters is the subject of German patent No. 1,124,483. According to this reference, alcohol cleavage, for example of β-methoxy propionic acid methyl ester of β-methoxy isobutyric acid methyl ester, follows by passing the esters over catalysts comprising aluminum oxide and oxides of the VI sub-group of the Periodic System at temperatures of 200°C. – 400°C. The yields of methylmethacrylate are given as over 95 percent.

The cleavage of water from β-hydroxy isobutyric acid methyl ester with the formation of methyl methacrylate is possible according to U.S. Pat. No. 2,208,355.

When complexes of vanadium are employed as the catalyst system, methyl succinic acid dimethyl ester is preferentially produced, as is especially to be seen from Examples 22 and 23. This can be used as such, advantageously as a solvent, or can be converted to methyl methacrylate by cleavage of carbon monoxide and methanol. According to U.S. Pat. No. 3,625,996, in this process catalysts are employed which are complexes of a platinum metal having organic phosphines, arsines, or stibines as ligands.

A better understanding of the present invention and of its many advantages will be had by referring to the following specific examples, given by way of illustration. In view of the considerable technical significance of methyl methacrylate and the polymers produced therefrom, the oxycarbonylation of propylene in methanol deserves particular emphasis, whether or not methyl methacrylate is produced directly or whether "pre-cursors" of this ester, described and shown in the specification and examples, are formed.

EXAMPLE 1

Bis-(titanium-IV-triacetate)-oxide, Anorg. Chem. 291, 97 (1957) is prepared from titanium tetramethylate and glacial acetic acid. 2 g of this compound are dissolved with 2 g of iron-III-chloride and 2 g of triphenyl phosphine oxide in 700 ml of methanol. Thereafter, about 10 atmospheres of propylene, 40 atmospheres of carbon monoxide, and 20 atmospheres of oxygen are introduced under pressure and heated to 160°C.

Distillation of the product gives:
1.3 g methylmethacrylate;
0.7 g of isobutyric acid methyl ester; and
0.2 g of crotonic acid methyl ester.

EXAMPLE 2

In a manner analogous to that of Dilthey, Chem. Ber. 37, 589 (1904), tris-(benzoyl acetonato)-titanium-IV-tetrachloroferrate is synthesized from 4.86 g of benzoyl acetone, 2.4 g of iron-III-chloride, and 1.9 g of titanium-IV-chloride in 25 ml of glacial acetic acid. The red-brown complex is isolated and combined with 5 g of triphenyl phosphine to form a catalyst. The procedure of Example 1 is then followed.

Working up of the product gives:
5.3 g of methylmethacrylate;
2.3 g of crotonic acid methyl ester; and
14.1 g of methyl succinic acid monomethyl and dimethyl esters.

EXAMPLE 3

0.8 g of vanadium-III-chloride and 2 g of copper-III-chloride are dissolved in 500 ml methanol and this solution is saturated with propylene. Then 80 atmospheres of carbon monoxide and 20 atmospheres of oxygen are further added and the mixture heated to 140°C.

2.2 g of methylmethacrylate;
0.5 g of crotonic acid methyl ester; and
16.7 g of methyl succinic acid dimethyl ester are obtained.

EXAMPLE 4

2 g of vanadium-III-chloride are dissolved in 600 ml of methanol. Then, 10 atmospheres of propylene, 40 atmospheres of carbon monoxide, and 25 atmospheres of air are introduced under pressure and the mixture is heated to 160°C.

2.6 g of methyl succinic acid dimethyl ester and 0.1 g of β-methoxy-isobutyric acid methyl ester are obtained.

EXAMPLE 5

2 of dihydroxo-hexaacetato-trichromium-III-diacetate [cf. G. Brauer, Handbuch der praep. anorgn. Chem., page 1027, Ferdinand Enke Verlag, Stuttgart (1954)] are dissolved with 2 g of copper-II-bromide and 5 g of triphenylphosphine in 600 ml of methanol. Thereafter, 10 atmospheres of propylene, 40 atmospheres of carbon monoxide, and 25 atmospheres of air are successively introduced under pressure and the mixture heated to 160°C.

1.5 g of β-methoxy-isobutyric acid methyl ester and 1.2 g of methyl succinic acid dimethyl ester are obtained.

EXAMPLE 6

Example 5 is repeated in ethanol. 1.2 g of β-hydroxyn-butyric acid ethyl ester, 0.6 g of β-ethoxy-n-butyric acid ethyl ester, and 0.5 g of methyl succinic acid diethyl ester are obtained.

EXAMPLE 7

Example 5 is repeated using 2 g of bis-triethyl phosphitechromium-II-chloride dissolved in 600 ml of are
1 g of methyl succinic acid dimethyl ester and 0.2 g of β-methoxy-isobutyric acid methyl ester was obtained.

EXAMPLE 8

Example 5 is repeated using 2 g of di-pyridino-dihydratodi-hydroxo-chromium-III-chloride (Gmelin, Vol. 52c, page 213).

0.5 g of methyl succinic acid dimethyl ester and 0.5 g of β-methoxy-isobutyric acid methyl ester are obtained.

EXAMPLE 9

Example 1 is repeated using 2 g of chromium-III-chloride, 2 g of cobalt-II-chloride, and 5 g of triphenylphosphine dissolved in 600 ml of methanol.

1.6 g of methyl succinic acid dimethyl ester and 1.4 g of β-methoxy-isobutyric acid methyl ester are obtained.

EXAMPLE 10

Example 1 is repeated using 4 g of nickel-dimethyl glyoximate, 4 g of hydrogen iodide, and 5 g of triphenyl phosphine dissolved in 600 ml of methanol.

2.3 g of methymethacrylate and 0.6 g of crotonic acid methyl ester are obtained.

EXAMPLE 11

2 g of chloro-pyridino-bis(dimethylglyoximato)-nickelII [cf. Chem. Ber. 97, 3061 (1964)] are employed as a catalyst and treated as in Example 1.

0.5 g of methylmethacrylate, 0.3 g of crotonic acid methyl ester, and 1.5 g of methyl succinic acid dimethyl ester are obtained.

EXAMPLES 12 – 17

The process of Example 5 is carried out in each case using 2 g of the following catalysts in the presence of the optional additive noted.

| Example | Catalyst | A (g) | B (g) | C (g) |
| --- | --- | --- | --- | --- |
| 12 | CuCl + P($C_6H_5$)$_3$ | 0.4 | 0.2 | 1.2 |
| 13 | CuBr$_2$ + [OP($C_6H_5$)$_3$]$_2$ | 1.5 | 0.2 | 1.5 |
| 14 | CuCl + [P(OCH$_3$)$_3$]$_2$ | 1.5 | — | 0.5 |
| 15 | CuBr + [P(OCH$_3$)$_3$]$_2$ | 1.0 | 0.1 | 0.5 |
| 16 | CuI + [P(OC$_4$H$_9$)$_3$]$_2$ | 1.5 | 0.1 | 0.5 |
| 17 | CuCl$_2$ + C$_5$H$_5$NO (pyridine oxide) | 0.1 | 0.1 | 1.0 |

A = methyl succinic acid dimethyl ester
B = β-methoxy-isobutyric acid methyl ester
C = β-hydroxy-n-butyric acid methyl ester

EXAMPLE 18

2 g of copper-II-bromide are dissolved in 600 ml of methanol. Thereafter, 20 atmospheres of ethylene, 40 atmospheres of carbon monoxide, and 25 atmospheres of air are introduced under pressure and the mixture is heated to 160°C.

1 g of succinic acid dimethyl ester and 0.2 g of β-methoxy-propionic acid methyl ester are obtained.

EXAMPLE 19

2.2 g of blue-violet bis-triphenyl phosphine oxide-vanadium-III-trichloride are prepared from 2.8 g of triphenyl phosphine oxide and 0.8 g of vanadium-III-chloride in ethanol [cf. Z. anorg. allg. Chem. 301, 195 (1959)]. The material is dissolved in 600 ml of methanol and saturated with propylene. Thereafter, 60 atmospheres of carbon monoxide and 40 atmospheres of compressed air are introduced under pressure and the mixture is heated to 170°C.

2.4 g of methyl succinic acid dimethyl ester and 2 g of β-hydroxy-n-butyric acid methyl ester are obtained.

EXAMPLE 20

A vanadium phosphine-oxide complex is prepared as in Example 19, from 0.25 g of vanadium-II-dichoride and 1.1 g of triphenyl phosphine oxide. 1.7 g of a dark mass containing dark green crystals are obtained. This complex is dissolved in methanol and treated as in Example 19.

0.65 g of methylmethacrylate, 0.4 g of crotonic acid methyl ester, and 3.2 g of methyl succinic acid methyl ester are obtained.

EXAMPLE 21

Analogous to the teaching of J. Inorg. Chem. 25, 637 (1963), chromium-trichloride-tris-triphenyl-phosphine oxide was prepared in ethanol from 1.58 g of anhydrous chromium-III-chloride and 8.34 g of triphenyl phosphine oxide. After evaporation of the ethanol, a syrup-like violet residue remained. This was dissolved in methanol and treated as in Example 19.

5.6 g of methyl succinic acid dimethyl ester are obtained.

EXAMPLE 22

Analogous to the teaching of Issleib [Z. anorg. allg. Chem. 301, 195 (1959)], bis-triphenyl phosphine-oxide-vanadiumtrichloride was prepared from 0.8 g of vanadium-III-chloride and 2.8 g of triphenyl phosphine oxide in 40 ml of bromobenzene. The precipitated blue-green crystals are dissolved in 500 ml of methanol and form a clear blue solution. The material is treated as in Example 19.

30.5 g of methyl succinic acid dimethyl ester are obtained.

EXAMPLE 23

0.9 g of vanadyl-V-trichloride are refluxed in 40 ml of dioxane for four hours together with 2.8 g of triphenyl phosphine oxide. After cooling, bright green crystals precipitate. These are vacuum filtered and dissolved in 500 ml of methanol. This material is treated as in the previous Example.

13 g of methyl succinic acid dimethyl ester are obtained.

EXAMPLE 24

1.5 g of magnesium tetramethoxy cuprate, prepared from copper methylate and magnesium methylate [Ann. 476, 113 (1929)] are dissolved together with 5.0 g of potassium bromide and 2 g of triphenyl phosphine in 700 ml of methanol. 6 atmospheres of propylene, 40 atmospheres of carbon monoxide, and 20 atmospheres of oxygen are introduced into the solution under pressure. After heating to 150°C., the pressure decreases slowly and on cooling still amounts to 19 atmospheres. Working up produces:

2.0 g methylmethacrylate;
5.1 g isobutyric acid methyl ester;
2.0 g n-butyric acid methyl ester;
7.4 g of crotonic acid methyl ester; and
74.0 g of methyl succinic acid monomethyl and dimethyl esters.

EXAMPLE 25

0.8 g of vanadium trichloride is refluxed for 2 hours in 40 ml of bromobenzene together with 1.0 g of pyridine-N-oxide. The dark-green somewhat greasy substance formed is vacuum filtered and is treated further as in Example 19.

0.5 g of methyl succinic acid dimethyl ester is obtained.

EXAMPLES 26 – 40

The process of Example 5 is carried out in each case using 2 g of the following catalysts, alone or in the presence of the optional additives noted:

| Example | Catalyst | A (g) | B (g) |
| --- | --- | --- | --- |
| 26 | CuBr$_2$ + [P(o-C$_6$H$_4$CH$_3$)$_3$]$_2$ | 1.2 | 0.5 |
| 27 | CuBr$_2$ + [P(m-C$_6$H$_4$CH$_3$)$_3$]$_2$ | 3.7 | 0.4 |
| 28 | CuBr$_2$ + [P(p-C$_6$H$_4$CH$_3$)$_3$]$_2$ | 1.7 | 0.2 |
| 29 | CuBr$_2$ + (ETPB)$_2$ | 0.6 | 0.2 |
| 30 | CuBr + P(n-C$_4$H$_9$)$_3$ | 1.5 | 0.2 |
| 31 | VCl$_2$ + [P(n-C$_4$H$_9$)$_3$]$_2$ | — | 0.8 |
| 32 | VOCl$_2$ + (C$_5$H$_5$N)$_2$ | — | 2.8 |
| 33 | VOCl$_3$ + [OP(CH$_2$OH)$_3$]$_2$ | — | 0.2 |
| 34 | CrCl$_2$ + [P(OC$_4$H$_9$)$_3$]$_3$ | — | 1.5 |
| 35 | VOCl$_3$ + [OP(C$_6$H$_5$)$_3$]$_2$ + 0.3 g NbCl$_2$(OCH$_3$)$_2$ | — | 1.5 |
| 36 | CuCl + AlCl$_3$ | 0.8 | 0.2 |
| 37 | CrBr$_3$ + [OP(C$_6$H$_5$)$_3$]$_3$ | — | 1.0 |
| 38 | Fe(CO)$_4$I$_2$ | — | 3.6 |
| 39 | CoBr$_2$ + [OP(C$_6$H$_5$)$_3$]$_2$ | — | 0.5 |
| 40 | CrCl$_3$ | — | 0.5 |

A = β-hydroxy-n-butyric acid methyl ester
B = methyl succinic acid dimethyl ester
ETPB = 1-ethyl-3,5,8-trioxa-4-phospha-bycyclo-(2,2,2)-octane,

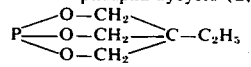

EXAMPLE 41

A multi-nuclear complex [cf. Chemische Berichte 41, 3241 (1908)] is formed from 1.0 g of chromium-VI-oxide and 5.05 g of cobalt-II-bromide in 25 ml of glacial acetic acid. 2 g of these blue-green crystals are dissolved in methanol and treated further as in Example 5.

0.5 g of methyl succinic acid dimethyl ester and 0.8 g of β-hydroxy butyric acid ester are obtained.

EXAMPLE 42

The process of Example 19 is repeated using 2 g of cobalt iodide. 0.5 g methyl succinic acid dimethylester is obtained.

EXAMPLE 43

Example 19 is repeated using 10 g nickel dibromide trihydrate. 1.3 g methyl succinic dimethylester is obtained.

What is claimed is:

1. In a method for the oxycarbonylation of ethylene or propylene by reacting ethylene or propylene, in methanol or ethanol as the reaction medium, at an elevated temperature and under pressure, with carbon monoxide and oxygen in the presence of a catalyst, the improvement wherein said catalyst consists essentially of a compound, soluble in the reaction medium under the reaction conditions, of a metal selected from the group consisting of vanadium, chromium, iron, cobalt, nickel, and copper, and of a chloride, bromide, or iodide of some other non-catalytic metal, or of hydrogen, if said compound is not a chloride, bromide, or iodide.

2. A method as in claim 1 wherein said catalytic metal compound is a chloride, bromide, or iodide.

3. A method as in claim 1 wherein said catalytic metal compound is other than a chloride, bromide, or iodide and a chloride, bromide, or iodide of some other non-catalytic metal, or of hydrogen, is present.

4. A process as in claim 1 wherein said catalyst is present in an amount of 0.01 to 5 percent by weight of the alcoholic reaction medium.

5. A process as in claim 1 wherein the reaction is carried out at a temperature from 80°C. to 300°C. under superatmospheric pressure.

6. A process as in claim 1 wherein propylene is oxycarbonylated in methanol.

7. In a method for the oxycarbonylation of ethylene or propylene by reacting ethylene or propylene, in methanol or ethanol as the reaction medium, at an elevated temperature and under pressure, with carbon monoxide and oxygen in the presence of a catalyst, the improvement wherein said catalyst consists essentially of a compound, soluble in the reaction medium under the reaction conditions, of a metal selected from the group consisting of vanadium, chromium, iron, cobalt, nickel, and copper, and of a chloride, bromide, or iodide of some other non-catalytic metal, or of hydrogen, if said compound is not a chloride, bromide, or iodide, and wherein a soluble compound of magnesium, aluminum, niobium or titanium is additionally present in said reaction medium.

8. A method as in claim 7 wherein said catalytic metal compound is a chloride, bromide, or iodide.

9. A method as in claim 7 wherein said catalytic metal compound is other than a chloride, bromide, or iodide and a chloride, bromide, or iodide of some other non-catalytic metal, or of hydrogen, is present.

10. A process as in claim 7 wherein said catalyst is present in an amount of 0.01 to 5 percent by weight of the alcoholic reaction medium.

11. A process as in claim 7 wherein the reaction is carried out at a temperature from 80°C. to 300°C. under superatmospheric pressure.

12. A process as in claim 7 wherein propylene is oxycarbonylated in methanol.

13. In a method for the oxycarbonylation of ethylene or propylene by reacting ethylene or propylene, in methanol or ethanol as the reaction medium, at an elevated temperature and under pressure, with carbon monoxide and oxygen in the presence of a catalyst, the improvement wherein said catalyst consists essentially of a compound, soluble in the reaction medium under the reaction conditions, of a metal selected from the group consisting of vanadium, chromium, iron, cobalt, nickel, and copper, and of a chloride, bromide, or iodide of some other non-catalytic metal, or of hydrogen, if said compound is not a chloride, bromide, or iodide, and wherein a member selected from the group consisting of phosphites, N-oxides, heterocyclic tertiary amines, phosphines, and phosphine oxides is additionally present in said reaction medium.

14. A method as in claim 13 wherein said catalytic metal compound is a chloride, bromide, or iodide.

15. A method as in claim 13 wherein said catalytic metal compound is other than a chloride, bromide, or iodide and a chloride, bromide, or iodide of some other non-catalytic metal, or of hydrogen, is present.

16. A process as in claim 13 wherein said catalyst is present in an amount of 0.01 to 5 percent by weight of the alcoholic reaction medium.

17. A process as in claim 13 wherein the reaction is carried out at a temperature from 80°C. to 300°C. under superatmospheric pressure.

18. A process as in claim 13 wherein propylene is oxycarbonylated in methanol.

19. A method as in claim 13 wherein said phosphite is a trialkylphosphite.

20. A method as in claim 13 wherein said phosphine is a trialkyl-, trialkylol-, triphenyl-, or tri(alkylphenyl)-phosphine.

21. A method as in claim 13 wherein said phosphine oxide is a trialkyl-, trialkylol-, triphenyl-, or tri(alkylphenyl)-phosphine oxide.

22. A process as in claim 13 wherein said heterocyclic tertiary amine is pyridine.

23. A process as in claim 13 wherein said N-oxide is pyridine N-oxide.

24. In a method for the oxycarbonylation of ethylene or propylene by reacting ethylene or propylene, in methanol or ethanol as the reaction medium, at an elevated temperature and under pressure, with carbon monoxide and oxygen in the presence of a catalyst, the improvement wherein said catalyst consists essentially of a compound, soluble in the reaction medium under the reaction conditions, of a metal selected from the group consisting of vanadium, chromium, iron, cobalt, nickel, and copper, and of a chloride, bromide, or iodide of some other non-catalytic metal, or of hydrogen, if said compound is not a chloride, bromide, or iodide, and wherein a soluble compound of magnesium, aluminum, niobium, or titanium, and a member selected from the group consisting of phosphites, N-oxides, heterocyclic tertiary amines, phosphines, and phosphine oxides are additionally present in said reaction medium.

25. A process as in claim 24 wherein said catalytic metal compound is a chloride, bromide, or iodide.

26. A process as in claim 24 wherein said catalytic metal compound is other than a chloride, bromide, or iodide and a chloride, bromide, or iodide of some other non-catalytic metal, or of hydrogen, is present.

27. A process as in claim 24 wherein said catalyst is present in an amount of 0.01 to 5 percent by weight of the alcoholic reaction medium.

28. A process as in claim 24 wherein the reaction is carried out at a temperature from 80°C. to 300°C. under superatmospheric pressure.

29. A process as in claim 24 wherein propylene is oxycarbonylated in methanol.

30. A method as in claim 24 wherein said phosphite is a trialkylphosphite.

31. A method as in claim 24 wherein said phosphine is a trialkyl-, trialkylol-, triphenyl-, or tri(alkylphenyl)-phosphine.

32. A method as in claim 24 wherein said phosphine oxide is a trialkyl-, trialkylol-, triphenyl-, or tri(alkylphenyl)phosphine oxide.

33. A process as in claim 24 wherein said heterocyclic tertiary amine is pyridine.

34. A process as in claim 24 wherein said N-oxide is pyridine N-oxide.

* * * * *